United States Patent
Fowler et al.

(10) Patent No.: US 10,004,223 B2
(45) Date of Patent: Jun. 26, 2018

(54) METHODS FOR GENERATING HIGH ASPECT-RATIO POLYMERIC PARTICLES COMPRISING AN ACTIVE INGREDIENT

(75) Inventors: Jeffrey Fowler, Greensboro, NC (US); Sejong Kim, Greensboro, NC (US)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days. days.

(21) Appl. No.: 13/509,528

(22) PCT Filed: Nov. 12, 2010

(86) PCT No.: PCT/US2010/056439
§ 371 (c)(1),
(2), (4) Date: Aug. 29, 2012

(87) PCT Pub. No.: WO2011/060210
PCT Pub. Date: May 19, 2011

(65) Prior Publication Data
US 2012/0329648 A1 Dec. 27, 2012

Related U.S. Application Data

(60) Provisional application No. 61/260,908, filed on Nov. 13, 2009.

(51) Int. Cl.
| | |
|---|---|
| *A01N 25/00* | (2006.01) |
| *A01N 25/24* | (2006.01) |
| *A01N 43/54* | (2006.01) |
| *A01N 43/82* | (2006.01) |
| *A01N 51/00* | (2006.01) |

(52) U.S. Cl.
CPC ............ *A01N 25/00* (2013.01); *A01N 25/24* (2013.01); *A01N 43/54* (2013.01); *A01N 43/82* (2013.01); *A01N 51/00* (2013.01)

(58) Field of Classification Search
CPC ......... A01N 25/00; A01N 25/24; A01N 25/10
See application file for complete search history.

(56) References Cited

U.S. PATENT DOCUMENTS

| | | | |
|---|---|---|---|
| 2006/0058502 A1* | 3/2006 | Doane et al. | 530/200 |
| 2006/0193882 A1* | 8/2006 | Botts et al. | 424/405 |
| 2007/0249498 A1 | 6/2007 | Van Der Drift | |

FOREIGN PATENT DOCUMENTS

| | | |
|---|---|---|
| WO | 2008/155907 | 12/2008 |
| WO | 201039865 | 4/2010 |

OTHER PUBLICATIONS

Li et al, "Mechanical Model of Micro-particle on Surface Adhesion." Environmental Science & Technology [online], 2008, additional citation information unavailable, Retrieved from the Internet: <URL: http:en.cnki.com.cn/Article_en/CJFDTOTAL-FJKS200801002.htm>, English Abstract of an Article published in the Chinese Language.

Alargova et al. "Scalable Synthesis of a New Class of Polymer Microrods by a Liquid?Liquid Dispersion Technique." Advanced Materials [online], Sep. 2004 [Retrieved on Dec. 29, 2010], vol. 16, Iss. 18, pp. 1650-1653, Retrieved from the Internet: <Retrieved from the Internet: <URL: http://onlinelibrary.wiley.com>.

Dement et al, "Fertilizer Particle Size, Crop Response to Phosphorus and Potassium in Potassium Phosphates Varying Widely in Particle Size." Journal of Agricultural and Food Chemistry [online], May 1963 [Retrieved on Dec. 29, 2010], vol. 11, Iss. 3. pp. 207-212, Retrieved from the Internet: <URL: http://pubs.acs.org>.

* cited by examiner

*Primary Examiner* — Michael B. Pallay
(74) *Attorney, Agent, or Firm* — James Cueva

(57) ABSTRACT

The present invention relates to methods for generating polymeric particles which comprise one or more active ingredients. The invention also relates to the use of such polymeric particles as a seed treatment. The present technology provides an improved seed treatment suitable for applying plant propagation materials. The seed treatment of the present technology includes the use of high aspect-ratio particles as a seed treatment. The present technology has been found to have advantageous properties associated with the seed treatment including increased adherence of the formulation to the seed and reduced tendency to dust off.

9 Claims, No Drawings

METHODS FOR GENERATING HIGH ASPECT-RATIO POLYMERIC PARTICLES COMPRISING AN ACTIVE INGREDIENT

This application is a 371 of International Application No. PCT/US2010/056439 filed Nov. 12, 2010, which claims priority to U.S. 61/260,908 filed Nov. 13, 2009, the contents of which are incorporated herein by reference.

The present invention relates to methods for generating polymeric particles which comprise one or more active ingredients. The invention also relates to the use of such polymeric particles as a seed treatment.

A seed treatment is any material applied to plant propagation material. Examples of seed treatments include, inter alia, pesticides, non-pesticide formularies, and mixtures thereof. Non-pesticide formularies generally include material such as surfactants, humectants, fillers, and polymers that influence the treated seed characteristics. Seed treatments are generally used on a large variety of crops to control a large variety of pests. Seed treatments are commonly used to ensure uniform stand establishment by protecting against soilborne diseases and insects. Systemic seed treatments may provide an alternative to traditional broadcast sprays of foliar fungicides or insecticides for certain early season airborne diseases and insects.

Plant propagation material, as defined herein, encompasses both true seeds and other plant propagation materials. While plant propagation material encompasses true seeds, plant propagation material itself is commonly referred to as a seed and is defined as such herein. Most seed treatments are applied to true seeds, which have a seed coat surrounding an embryo. Seed treatments are also applied to other plant propagation materials such as rhizomes, bulbs, corms or tubers.

Obtaining thorough seed coverage can be difficult when attempting to treat seed. For example, dry formulations can present unacceptable worker exposure to the fungicidal or insecticidal active ingredient. Alternatively with liquid formulation problems can arise such as unacceptable drying times, material build-up in the seed treater, low seed flowability, poor seed coverage and dust-off of the pesticide from the seed prior to planting. As a result, handling is rendered difficult and the biological efficacy of the seed treatment may be reduced.

Another limitation of conventional seed treatment formulations is that the active ingredients are available for rapid dissolution in soil moisture after the seed has been planted. In some cases this can result in phytotoxic injury to the growing plant, or an undesirably short period of pest control.

The present technology provides for compositions having improved adherence to plant propagation material with low dust-off. The compositions of the present technology have particular application in the protection of plant propagation materials and the resulting plant against pests when combined with one or more pesticides.

The present technology thus provides an improved seed treatment suitable for applying plant propagation materials. The seed treatment of the present technology includes the use of high aspect-ratio particles as a seed treatment. The present technology has been found to have advantageous properties associated with the seed treatment including: increased adherence of the formulation to the seed and reduced tendency to dust off.

The present technology also provides for reduced uptake into the treated seed as compared to conventional seed treatments. Such an advantage provides for increased germination and vigour of the plant seed and/or resulting plant.

Other advantages include an increased active ingredient loading without causing injury to the seed or plant, and a controlled release of active ingredient over a longer period of time than is possible with conventional seeds.

The present technology also provides for improved treatment efficiency and working conditions through the increased adherence of the formulation to the seed. Increased adherence to the seed during and after drying results in a reduction of dust-off. A reduction in dust-off results in cleaner seed treatment machinery, which reduces downtime in the necessity of the cleaning the machinery. A reduction in dust-off also results in improved working conditions for workers.

According to the present technology there is provided a method for generating high aspect-ratio polymeric particles comprising an active ingredient, comprising: (a) generating a solution (1) which comprises dissolved polymer and/or polymerisable or cross-linkable monomers and dissolved and/or dispersed active ingredient in a first solvent; and (b) adding said solution to a further solvent or mixture of solvents (2) wherein said polymer, monomers and said active ingredient are substantially insoluble in said further solvent or mixture of solvents; and (c) precipitating the polymer or monomers from the solution wherein said active ingredient is substantially confined within the precipitate, and then polymerising the monomers if such are present. The skilled person will recognise that the method of the present invention includes a variation wherein in step (b) the solvent is added to the solution rather than the solution added to the solvent. The solvent and further solvent according to the invention are fully miscible and a solute or surfactant may be present in said further solvent in order to achieve the requisite miscibility and polymer wettability as described below, all of which will be apparent to the person skilled in the art. In particular the method of adding the solution to the solvent or mixture of solvents is performed by continuously injecting a jet or stream of the solution into a stirred vessel or flow stream of the solvent or mixture of solvents, such that the precipitated polymer or optionally monomers and said active ingredient forms into solid particles of high aspect ratio.

Synthesis of the high aspect-ratio polymeric particles are also described in the article, *Scalable Synthesis of a New Class of Polymer Microrods by a Liquid-Liquid Dispersion Technique*, Alargova R G, Bhatt K H, Paunov V N, Velev O D, Adv. Mater., 16, 1653-7 (2004), the contents of which are herein incorporated by reference.

High aspect-ratio polymeric particle means a substantially flat or substantially rod-like particle with a shortest dimension of between about 0.05 to 10 microns, and longest dimension of between about 1 and 1000 microns, and the aspect ratio of the shortest to longest dimension is at least about 1:10. The polymeric particles of the invention may be made of, for example, epoxy resin; polyacrylate or derivatives; vinyl; polyester; polyurethane; polyurea; polyethylene; polypropylene or any other like polymer that would be considered suitable by the person skilled in the art. The polymeric particles may be polymer-based, monomer-based or non-crystalline based.

In a particular embodiment of the invention epoxy resin SU-8 is dissolved in a solvent such as ethyl lactate. Following addition of the active ingredient to this solution it may be added to a further solvent which comprises glycerin.

In a further embodiment of the invention polymethylmethacrylate is dissolved in a solvent such as acetone. Following addition of the active ingredient to this solution it may be added to a further solvent which comprises water, which may additionally contain surfactants.

In a further embodiment of the invention polystyrene is dissolved in an aromatic petroleum distillate solvent such as Aromatic 200 (Exxon-Mobil). Following addition of the active ingredient to this solution it may be added to a further solvent which comprises a 1:1 mixture of propylene glycol and dimethyl lactamide.

In a further embodiment of the invention poly (butyl acrylate-co-ethyl acrylate-co-methacrylic acid) is dissolved in a solvent such as ethanol. Following addition of the active ingredient to this solution it may be added to a further solvent which comprises a 3:2 mixture of water and glycerol.

In one embodiment of the invention the polymer and/or polymerisable or cross-linkable monomers are dissolved into the solution such that the dissolved polymer and/or polymerisable or cross-linkable monomers form at least about 1% of the solution. In a further embodiment, the dissolved polymer and/or polymerisable or cross-linkable monomers form at least about 10% of the solution.

The present invention further provides a method as described above wherein at least 75% of the active ingredient is confined within the precipitate. In a further embodiment at least 80% of the active ingredient is confined within the precipitate. In a further embodiment at least 85% of the active ingredient is confined within the precipitate. In a further embodiment at least 90% of the active ingredient is confined within the precipitate. In a further embodiment at least 95% of the active ingredient is confined within the precipitate.

The present invention still further provides a method as described above wherein the precipitate is constituted substantially by polymerised monomers.

The present invention still further provides a method as described above wherein polymerisation of the monomers in the polymeric particles is further facilitated via UV light and/or reaction at elevated temperature.

The present invention still further provides a method as described above wherein a polyfunctional amine is added to further facilitate polymerisation of said monomers in the polymeric particles. In one embodiment said amine is added to the further solvent or mixture of solvents.

The present invention still further provides a method as described above wherein said further solvent or mixture of solvents further facilitates polymerisation of said monomers in the polymeric particles.

In a further aspect of the invention there is provided a method for generating high aspect-ratio polymeric particles comprising an active ingredient said method comprising (a) generating a solution (1) by dissolving and/or dispersing an active ingredient in a first solvent which comprises dissolved polymer and/or polymerisable monomers; (b) combining said solution with a further solvent or mixture of solvents (2) to produce a further solution wherein said polymer and monomers and said active ingredient are substantially insoluble in said further solvent or mixture of solvents; (c) precipitating said polymer and optionally the monomers into polymeric particles which confine said active ingredient. The solution may be combined with a further solvent or mixture of solvents by simply pouring the former into the latter, or by injecting the former into the latter through a tube having an opening below the surface of the liquid, and where the solvent or mixture of solvents is swept past the addition point such that the incoming stream of solution is subjected to extensional flow deformation, for example via a pump or a rotary mixing device, such as a mechanical stirrer. With respect to the methods throughout this specification the solution (1) and the solvent or mixture of solvents (2) can also be mixed via mixing methods well known to the person skilled in the art.

In a particular embodiment the invention provides a method as described herein wherein solution (1) is injected into the solvent or mixture of solvents (2) or vice versa. In a preferred embodiment said solution (1) is injected into the solvent or mixture of solvents (2).

In a particular embodiment of the invention as described above, the interfacial tension between said polymer and said further solvent is sufficient to ensure that once formed the polymeric particles have a shortest dimension of between about 0.05 to 10 microns, and a longest dimension of between about 1 and 1000 microns, and the aspect ratio of the shortest to longest dimension is at least about 1:10.

In a still further embodiment there is provided a method as described above wherein when said polymer is precipitating into the polymeric particles, the contact angle of the further solvent wetting said polymeric particle is less than or equal to about 90°. In a further embodiment said contact angle is less than or equal to about 70°. In a still further embodiment said contact angle is less than or equal to about 50°. In a still further embodiment said contact angle is less than 50°. During formation of the polymeric particles in accordance with the methods of the invention, the polymeric particles are wetted via contact with the further solvent within the solution in which the polymeric particles are formed. If the polymeric particles form contact with the further solvent via an angle as described above the polymeric particles are capable of retaining a high aspect ratio for a greater period of time and are therefore more stable. The person skilled in the art is capable of selecting an appropriate combination of dissolved polymer and further solvent such that upon precipitation and formation of the polymeric particles, the contact angle as mentioned above is achieved.

The present invention still further provides a method as described above wherein the first solvent and further solvent are fully miscible.

In a particular embodiment of the invention said polymeric particles are harvested from said further solution.

The active ingredient containing high aspect-ratio polymeric particles according to the invention may also be generated via other methods which are known in the art for the generation of the high aspect-ratio polymeric particles per se, wherein such prior art methods are modified to allow for the inclusion of the active ingredient so that the active ingredient becomes incorporated in the high aspect-ratio polymeric particles. Examples of alternative high aspect-ratio polymeric particles synthesis methods include, electro spinning which is well known to the person skilled in the art.

In addition, the high aspect-ratio polymeric particle may be generated via dissolving and/or dispersing the active ingredient in a polymer melt. The active ingredient containing melt may then be emulsified via a conventional means, (such as surfactant stabilised, colloidally stabilised or maintained temporarily via mechanical agitation), into a heated further solvent. Whilst the emulsion is subjected to an extensional flow deformation, it is cooled below the solidification temperature of the polymer such that the stretched droplets form solid high aspect-ratio polymeric particles. This method obviates the need to dissolve or disperse the active ingredient in a solvent as per the method described above.

A still further method to generate the high aspect-ratio polymeric particle involves dissolving and/or dispersing the active ingredient in a solution which comprises monomers which can be subsequently cross-linked into polymer. The solution may be stirred into water which optionally contains a solute and the solution may be emulsified using emulsifiers known to the person skilled in the art. The resulting emulsion may then be subjected to an extensional flow deformation wherein the monomers may be cross-linked to form the solid high aspect-ratio polymeric particles. Such cross-linking may be achieved via the methods well known in the art and applicable to the monomers used in the method.

In a further aspect of the technology there is provided a method for treating plant propagation material comprising: (a) generating high aspect-ratio polymeric particles which comprise an active ingredient and (b) applying said high aspect-ratio polymeric particles to the plant propagation material.

In a further aspect of the technology there is provided an article of manufacture comprising: plant propagation material treated with high aspect-ratio polymeric particles comprising an active ingredient.

In a further aspect of the invention there is provided a method of controlling, preventing or reducing pest damage to plant propagation material or a plant by: (a) generating high aspect-ratio polymeric particles which comprises an active ingredient; and (b) applying said particles to plant propagation material.

The high aspect-ratio polymeric particles containing the active ingredient may be generated as described in this specification or other known methods in the art.

The present invention still further provides a method as described above wherein said active ingredient is selected from the group consisting of: fungicide, herbicide, insecticide, molluscicide, arachnidicide, nematicide, bactericide and viricide.

In a particular embodiment of said method said ingredient is a fungicide. In a further embodiment said fungicide comprises a strobilurin or a strobilurin type fungicide.

Strobilurin and strobilurin-type fungicides are a well-known class of fungicides that act by inhibiting mitochondrial respiration by blocking electron transfer between cytochrome b and cytochrome $c_1$ at the ubiquinol oxidising site. They include the methoxyacrylate strobilurins such as azoxystrobin and picoxystrobin, the oximinoacetate strobilurins such as kresoxim-methyl and trifloxystrobin, the oximinoacetamide strobilurins such as dimoxystrobin, metominostrobin, orysastrobin (BAS 520) and the strobilurin of the formula:

the dihydrodioxazine strobilurins such as fluoxastrobin, the methoxycarbamate strobilurins such as pyraclostrobin, the strobilurin of the formula:

the imidazolinones strobilurin-types such as fenamidone, and the oxazolidinedione strobilurin-types such as famoxadone. Of particular interest is azoxystrobin. Azoxystrobin is also described as entry 47 in The Pesticide Manual, Thirteenth Edition, published by The British Crop Protection Council, 2003. Picoxystrobin is also described in the Pesticide Manual as entry 647.

In a further embodiment said fungicide is selected from the group consisting of: Azoxystrobin; Thiabendazole; Fludioxonil and a mixture thereof.

Fludioxonil is listed as entry 368 The Pesticide Manual, Fludioxonil is mainly known as a fungicide for use on crops and also as a seed treatment. Thiabendazole is listed as entry 790.

The high aspect-ratio polymeric particles according to the invention may comprise a single active ingredient or a combination of active ingredients. Where the fibres contain a single active ingredient, they may be mixed with other high aspect-ratio polymeric particles containing a different active ingredient to generate a mixture of particles containing the different active ingredients. The high aspect-ratio polymeric particles may be combined with one or more additives to improve particular properties (for example distribution on surfaces). Such additives are well known to the person skilled in the art. These may be blended with other bio-enhancing adjuvants (ingredients which may aid or modify the action of the active ingredient used in the high aspect-ratio polymeric particles of the invention).

Examples of other fungicides which may be used in accordance with the present invention include:
AC 382042 (N-(1-cyano-1,2-dimethylpropyl)-2-(2,4-dichlorophenoxy) propionamide), acibenzolar-S-methyl, alanycarb, aldimorph, anilazine, azaconazole, azafenidin, benalaxyl, benomyl, benthiavalicarb, biloxazol, bitertanol, blasticidin S, boscalid (new name for nicobifen), bromuconazole, Bronopol, bupirimate, captafol, captan, carbendazim, carbendazim chlorhydrate, carboxin, carpropamid, carvone, CGA 41396, CGA 41397, chinomethionate, chlorbenzthiazone, chlorothalonil, chlorozolinate, clozylacon, copper containing compounds such as copper oxychloride, copper oxyquino-late, copper sulphate, copper tallate, and Bordeaux mixture, cyamidazosulfamid, cyazofamid (IKF-916), cyflufenamid, cymoxanil, cyproconazole, cyprodinil, debacarb, di-2-pyridyl disulphide 1,1'-dioxide, dichlofluanid, diclocymet, diclomezine, dicloran, diethofencarb, difenoconazole, difenzoquat, diflumetorim, diiodomethyl-p-tolylsulfone (Amical, from Dow) O,O-di-iso-propyl-S-benzyl thiophosphate, dimefluazole, dimetconazole, dimethirimol, dimethomorph, dimoxystrobin, diniconazole, dinocap, dithianon, Dithiocarbamates, dodecyl dimethyl ammonium chloride, dodemorph, dodine, doguadine, edifenphos, epoxiconazole, ethaboxam, ethirimol, ethyl (Z)—N-benzyl-N ([methyl(methyl-thioethylideneaminooxycarbonyl)amino] thio)-β-alaninate, etridiazole, famoxadone, fenamidone, fenarimol, fenbuconazole, fenfuram, fenhexamid, fenoxanil (AC 382042), fenpropidin, fenpropimorph, fentin acetate, fentin hydroxide, ferbam, ferimzone, fluazinam, flumetover, flumorph, fluoroimide, fluoxastrobin, fluquinconazole, flusilazole, flusulfamide, flutolanil, flutriafol, folpet, fosetyl-aluminium, fuberidazole, furalaxyl, furametpyr, guazatine, hexaconazole, hydroxyisoxazole, hymexazole, imazalil, imibenconazole, iminoctadine, iminoctadine triacetate, 3-iodo-2-propynyl butylcarbamate (IBPC), ipconazole, iprobenfos, iprodione, iprovalicarb, isopropanyl butyl carbamate, isoprothiolane, kasugamycin, kresoxim-methyl, LY186054, LY211795, LY 248908, mancozeb, maneb, MBT mefenoxam, mepanipyrim, mepronil, metalaxyl, metalaxyl M, metconazole, metiram, metiram-zinc, metominostrobin, metrafenone, MON65500 (N-allyl-4,5-dimethyl-2-trimethylsilylthiophene-3-carboxamide), myc-lobutanil, NTN0301, neoasozin, nickel dimethyldithiocarbamate, nitrothale-isopropyl, nuarimol, 2-0-octyl-4-isothiazolin-3-one (Skane M 8 Rohm& Hass), ofurace, organomercury compounds, orysastrobin, oxadixyl, oxasulfuron, oxolinic acid, oxpoconazole, oxycarboxin, pefurazoate, penconazole, pencycuron, phenazin oxide, phosphorus acids, phthalide, picoxystrobin, polyoxin D, polyram, probenazole, prochloraz, procymidone, propamocarb, propamocarb hydrochloride, propiconazole, propineb, propionic acid, proquinazid, prothioconazole, pyraclostrobin, pyrazophos, Sodium and Zinc Pyrithione (Omadine chemistry from Arch Chem.), pyrifenox, pyrimethanil, pyroquilon, pyroxyfur, pyrroInitrin, quaternary ammonium compounds, quinomethionate, quinoxyfen, quintozene, silthiofam (MON 65500), S-imazalil, simeconazole, sipconazole, sodium pentachlorophenate, spiroxamine, streptomycin, sulphur, tebuconazole, tecloftalam, tecnazene, tetraconazole, thifluzamide, 2-(thiocyano-methylthio)benzothiazole, thiophanate-methyl, thiram, tiadinil, timibenconazole, tolclofos-methyl, tolylfluanid, triadimefon, triadimenol, triazbutil, triazoxide, tricyclazole, tridemorph, trifloxystrobin, triflumizole, triforine, triticonazole, validamycin A, vapam, vinclozolin, XRD-563, zineb, ziram, zoxamide and compounds of the formulae:

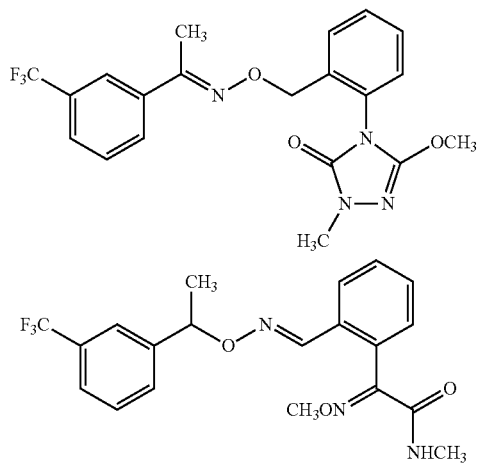

Examples of insecticides which may be used in accordance with the present invention include:
a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;
b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;
c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;
d) Benzoyl ureas, such as diflubenzuron, triflumuron, hexaflumuron, flufenoxuron or chlorfluazuron;
e) Organic tin compounds, such as cyhexatin, fenbutatin oxide or azocyclotin;
f) Pyrazoles, such as tebufenpyrad and fenpyroximate;
g) Macrolides, such as avermectins or milbemycins, for example abamectin, emamectin benzoate, ivermectin, milbemycin, spinosad or azadirachtin;
h) Hormones or pheromones;
i) Organochlorine compounds such as endosulfan, benzene hexachloride, DDT, chlordane or dieldrin;
j) Amidines, such as chlordimeform or amitraz;
k) Fumigant agents, such as chloropicrin, dichloropropane, methyl bromide or metam;
l) Chloronicotinyl compounds such as imidacloprid, thiacloprid, acetamiprid, nitenpyram or thiamethoxam;
m) Diacylhydrazines, such as tebufenozide, chromafenozide or methoxyfenozide;
n) Diphenyl ethers, such as diofenolan or pyriproxifen;
o) Indoxacarb;
p) Chlorfenapyr;
q) Pymetrozine;
r) Spirotetramat, Spiromesifen; sulfloxaflor or
s) Flubendiamid or Rynaxypyr.

Examples of herbicides which may be used in accordance with the present invention include:
2,3,6-TBA; 2,4-D; 2,4-DB; acetochlor; acifluorfen-sodium; aclonifen; acrolein; alachlor; alloxydim; ametryn; amicarbazone; amidosulfuron; aminopyralid; aminotriazol; amitrole ammonium sulfamate; anilofos; asulam; atrazine; aviglycine; azafenidin; azimsulfuron; BAY FOE 5043; beflubutamid; benazolin; bencarbazone; benfluralin; benfuresate; bensulfuron-methyl; bensulide; bentazone; benzfendizone; benzobicyclon; benzofenap; bialaphos; bifenox; bispyribac-sodium; borax; bromacil; bromobutide; bromophenoxim; bromoxynil; butachlor; butafenacil; butamifos; butralin; butroxydim; butylate; cafenstrole; carbetamide; carfentrazone-ethyl; chloransulam methyl; chlorbromuron; chlorflurenol-methyl; chloridazon; chlorimuron-ethyl; chloroacetic acid; chlorotoluron; chlorpropham; chlorsulfuron; chlorthal-dimethyl; cinidon-ethyl; cinmethylin; cinosulfuron; clefoxydim profoxidim; clethodim; clodinafop-propargyl; clomazone; clomeprop; clopyralid; cloransulam; cloransulam-methyl; cumuluron; cumyluron; cyanamide; cyanazine; cyclanilide; cycloate; cyclosulfamuron; cycloxydim; cyhalofop; cyhalofop-butyl; cyprosulfamide; daimuron; dalapon; dazomet; desmedipham; desmetryn; dicamba; dichlobenil; dichlorprop; dichlorprop-P; diclofop-methyl; diclosulam; difenzoquat metilsulfate; difufenican; diflufenzopyr; dimefuron; dimepiperate; dimethachlor; dimethametryn; dimethenamid; dimethenamid-P; dimethipin dimethylarsinic acid; dinitramine; dinoterb;

diphenamid; dipropetryn; diquat dibromide; dithiopyr; diuron; DNOC; DSMA; endothal; EPTC; esprocarb; ethalfluralin; ethametsulfuron-methyl; ethephon; ethofumesate; ethoxyfen-ethyl; ethoxysulfuron etobenzanid; fenclorim; fenoxaprop-P-ethyl; fentrazamide; ferrous sulfate; flamprop; flamprop-M; flazasulfuron; florasulam; fluazifop-butyl; fluazifop-P-butyl; fluazolate; flucarbazone sodium; flucetosulfuron; fluchloralin; flufenacet; flufenpyr-ethyl; flumetralin; flumetsulam; flumiclorac-pentyl; flumioxazin; flumipropin; fluometuron; fluoroglycofen-ethyl; fluoxaprop; flupoxam; flupropacil; flupropanate; flupyrsulfuron-methyl-sodium; flurenol; fluridone; fluorochloridone; fluoroxypyr; flurtamone; fluthiacet-methyl; fluxofenim; fomesafen; foramsulfuron; fosamine; glufosinate-ammonium; glyphosate; halosulfuron-methyl; haloxyfop; haloxyfop-P; HC-252; hexazinone; imazamethabenz-methyl; imazamox; imazapic; imazapyr; imazaquin; imazethapyr; imazosulfuron; indanofan; iodosulfuron; iodosulfuron-methyl-sodium; ioxynil; isopropazol; isoproturon; isouron; isoxaben; isoxachlortole; isoxadifen; isoxaflutole; Isoxapyrifop; karbutylate; KIH-485; lactofen; lenacil; linuron; MCPA; MCPA-thioethyl; MCPB; mecoprop; mecoprop-P; mefenacet; mefenpyr diethyl; mefluidide; mesosulfuron methyl; mesotrione; metam; metamifop (mefluoxafop); metamitron; metazachlor; methabenzthiazuron; methazole; methyl isothiocyanate; methylarsonic acid; methyldymron; metobenzuron; metobromuron; metolachlor; metosulam; metoxuron; metribuzin; metsulfuron-methyl; MK-616; molinate; monolinuron; MSMA; naproanilide; napropamide; naptalam; NDA-402989; neburon; nefenacet; nicosulfuron; nipyraclofen; n-methyl-glyphosate; nonanoic acid; norflurazon; oleic acid (fatty acids); orbencarb; orthosulfamuron; oryzalin; oxaciclomefone; oxadiargyl; oxadiazon; oxasulfuron; oxaziclomefone; oxyfluorfen; paraquat dichloride; pebulate; pendimethalin; penoxsulam; pentachlorophenol; pentanochlor; pentoxazone; pethoxamid; petrolium oils; phenmedipham; phenoxaprop-P-ethyl (R); picloram; picolinafen; pinoxaden; piperophos; pretilachlor; primisulfuron; primisulfuron-methyl; procarbazone; prodiamine; profluazol; profoxydim; prohexcadion calcium; prometon; prometryn; propachlor; propanil; propaquizafop; propazine; propham; propisochlor; propoxycarbazone; propoxycarbazone-sodium; propyzamide; prosulfocarb; prosulfuron; pyraclonil; pyrazogyl; pyraflufen-ethyl; pyrasulfotole; pyrazolynate; pyrazosulfuron-ethyl; pyrazoxyfen; pyribenzoxim; pyributicarb; pyridafol; pyridate; pyriftalid; pyriminobac-methyl; pyrimisulfan; pyrithiobac-sodium; quinclorac; quinmerac; quinoclamine; quizalofop; quizalofop-P; rimsulfuron; sequestren; sethoxydim; siduron; simazine; simetryn; S-metolachlor; sodium chlorate; sulcotrione; sulfentrazone; sulfometuron-methyl; sulfosate; sulfosulfuron; sulfuric acid; tar oils; TCA-sodium; tebutam; tebuthiuron; tefuryltrione; tembotrione; tepraloxydim; terbacil; terbumeton; terbuthylazine; terbutryn; thenylchlor; thiazafluoron; thiazimin; thiazopyr; thiencarbazone; thifensulfuron-methyl (thiameturon-methyl); thiobencarb; tiocarbazil; topramezone; tralkoxydim; tri-allate; triasulfuron; triaziflam; tribenuron-methyl; triclopyr; trietazine; triflosulam; trifloxysulfuron; trifloxysulfuron-sodium; trifluralin; triflusulfuron-methyl; trinexapac-ethyl; tritosulfuron; and urea sulfate.

The high aspect-ratio polymeric particles of the invention which contain a fungicide may be used in the prevention and/or treatment of growth of a number of fungi including the following: *Alternaria alternata, Aspergillus flavus, Aspergillus terreus, Aspergillus fumigatus, Aspergillus repens, Aspergillus versicolor, Candida albicans, Chaetomium globosum, Cladosporium cladosporioides, Cladosporium herbarum, Cladosporium sphaerospermum, Coniophora puteana, Curvularia genticulata, Diplodia natalensis, Epidermophyton floccosum, Fusarium oxysporum, Gliocladium vixens, Gloeophyllum trabeum, Humicola grisea, Lecythophora mutabilis, Lentinus cyathiformis, Lentinus lepidus, Memnionella echinata, Mucor indicus, Mucor racemosus, Oligoporus placenta, Paecilomyces variotii, Penicillium citrinum, Penicillium funiculosum, Penicillium ochrochloron, Penicillium purpurogenum, Penicillium pinophilum, Penicillium variabile, Petriella setifera, Phanerochaete chrysosporium, Phoma violacea, Poria placenta, Rhodotorula rubra, Schizophyllum commune, Sclerophoma phytiophila Scopulariopsis brevicaulis, Serpula lacrymans, Sporobolomyces roseus, Stemphylium dendriticum, Trichophyton mentagrophytes, Trichurus spiralis, Trichophyton rubrum, Ulocladium atrum* and *Ulocladium chartarum*.

It is particularly preferable to generate polymeric particles containing a fungicide for incorporation into a material, which fungicides are effective against the following fungi: *Alternaria alternata, Alternaria tenuissima, Aspergillus niger, Aspergillus versicolor, Aureobasidium pullulans, Chaetomium globosum, Cladosporium cladosporioides, Coniophora puteana, Gloeophyllum trabeum, Memnionella echinata, Mucor indicus, Oligoporus placenta, Penicillium citrinum, Penicillium chrysogenum, Penicillium funiculosum, Penicillium pinophilum, Sclerophoma phytiophila, Stachybotrys atra, Stachybotrys chartarum*, and *Ulocladium chartarum*.

The invention will now be described with reference to the following examples:

EXAMPLES

Example 1: Non-Aqueous Solvent System 324 g of epoxy resin SU-8 was dissolved in ethyl lactate. To this solution were added 72.9 g of azoxystrobin, 7.29 g of fludioxonil and 72.9 g of thiabendazole. The first two active ingredients went fully into solution while the latter active ingredient remained partly as a fine particulate suspension. A polymeric particle suspension was prepared by adding 109 g of this solution to 5050 g of glycerin under vigorous agitation.

Example 2: Water-Based Solvent System 2 g of polymethylmethacrylate was dissolved in 18 g of acetone. To this solution was added 0.2 g each of thiabendazole and azoxystrobin, and 0.02 g of fludioxonil. A polymeric particle suspension was prepared by adding 20 g of this suspension to 1500 mL of water under vigorous agitation.

Example 3: Filter Cake Product

A polymeric particle preparation prepared according to the method of example 1 was concentrated by vacuum filtration on a paper filter disk in a conventional Buchner funnel. The polymeric particles could be re-dispersed into an aqueous dispersion by stirring the filter cake vigorously into water.

Example 4: Polystyrene Particles Containing Thiamethoxam

Thiamethoxam powder 5 g was added and mixed to a solution of polystyrene 10 g in 85 g of Aromatic 200 petroleum distillate solvent. Once a homogeneous dispersion (I) was obtained, the dispersion (20 g) was dropwise added into an anti-solvent of propylene glycol (500 g) and dimethyl lactamide (500 g) mixture, where the anti-solvent was stirred by mechanical rotor (II). Subsequently, the dispersions (II) of polymer long-fibers were chopped by Turrex blender for 2 min at 5000 rpm. The resulting polymer particles were separated from the solvents by centrifugation and then re-dispersed in water containing surfactant (0.5 g of Rodasurf BC-610) to form 25 ml (III). The resulting polymer particles dispersion (III) was observed under a polarized optical microscopy, where mostly rod-shaped polymer particles of a few microns to several hundred micron length were found. It was also confirmed that thiamethoxam crystals were well distributed within the polymer particles and that they had high aspect ratio exceeding about 10.

Example 5: Poly (Butyl Acrylate-Co-Ethyl Acrylate-Co-Methacrylic Acid) Particles Containing Thiamethoxam Thiamethoxam powder 10 g was added to a solution of PBEM (Poly (butyl acrylate-co-ethyl acrylate-co-methacrylic acid)) 20 g in ethanol 70 g, and were mixed until homogeneous dispersion (I) was obtained. The dispersion (I) (20 g) was dropwise added into an anti-solvent of glycerin (400 g) and water (600 g) mixture, where the anti-solvent was stirred by mechanical rotor (II). Subsequently, the mixture (II) of polymer long-fibers was blended by Turrex for 2 min at 5000 rpm, in order to chop the long fibers. The chopped polymer fibers were separated from the solvents by centrifugation and then re-dispersed in water containing surfactant (0.5 g of Rodasurf BC-610) to form 40 ml (III). The resulting polymer particles were observed under a polarized optical microscopy. A variety of polymeric rods, shreds or platelets of a few micron to several hundred micron size were found. It was also confirmed that thiamethoxam crystals were well distributed within the polymer particles and that they had high aspect ratio exceeding about 10.

Example 6: Seed Treatments 100 g samples of corn seeds were coated with each of the liquid pesticide formulation compositions as follows:
A. Preparation of example 5 0.75 g, polymer binder (Flo Rite 1197, Becker Underwood) 0.2 g, and pigment (Colorcoat Red, Becker Underwood) 0.05 g
B. Preparation of example 5 1.5 g, Flo Rite 1197 0.4 g, and Colorcoat Red 0.1 g
C. Preparation of example 4 0.75 g, Flo Rite 1197 0.2 g, and Colorcoat Red 0.05 g
D. Preparation of example 4 0.65 g, Flo Rite 1197 0.3 g, and Colorcoat Red 0.05 g
E. (Control) Cruiser 5FS 0.4 g, Flo Rite 1197 0.25 g, Colorcoat Red 0.05 g and water 0.3 g Example 7: Dust Off The amount of dust detached from the corn seeds of example 6 was recorded. 50 g of corn seeds coated with pesticide formulations described above were placed in the rotary chamber (Rotavapor Buchi, Switzerland) connected to a vacuum line. As the chamber rotates at 50 rpm for 5 min, the dusts are collected at a filter paper placed at the connector to vacuum line. The mass increase of the filter paper after the seed chamber rotation experiment was recorded as the amount of dust off.

| Seed Coating | Dust off [mg/50 g seed] |
|---|---|
| Example 6A | 0.05 |
| Example 6C | 1.75 |
| Example 6D | 1.1 |
| Control 6E | 2.25 |

This example shows that the high aspect ratio particles have good adherence to seeds during handling and show improved dust off.

Example 8: Controlled Release 20 kernels of corn seeds prepared above (Example 6) were added to a bottle containing 100 g of deionized water. To enhance the solution uniformity, the water was gently stirred without moving seeds. The concentration of thiamethoxam in water was monitored as a function of time by HPLC and is given here as a percentage of the total AI recovered after 4 days stirring.

| Stir time | Example 6A | Example 6B | Example 6C | Control 6E |
|---|---|---|---|---|
| 1 hr | 69% | 87% | 67% | 95% |
| 3 hr | 71% | 91% | 69% | 96% |
| 1 day | 71% | 92% | 69% | 96% |
| 2 day | 71% | 93% | 69% | 98% |
| 3 day | 74% | 100% | 82% | 99% |
| 4 day | 100% | 100% | 100% | 100% |

This example illustrates that the polymeric particles give sustained release of active ingredient over several hours whereas the control seed treatment has essentially complete active ingredient release in less than one hour.

The invention claimed is:
1. A method comprising:
applying high-aspect ratio polymeric particles to a plant seed, wherein the high-aspect ratio polymeric particles have a shortest dimension and a longest dimension, and where the shortest dimension is between about 0.05 micron to 10 microns, and the longest dimension is between about 1 and 1000 microns; and wherein the polymeric particles comprise a polymer that is an epoxy, polymehtylmethacrylate, poly(butyl acrylate-co-ethyl acrylate-co-methacrylic acid), or polystyrene.
2. The method of claim 1 wherein the polymeric particles comprise a pesticidally active ingredient.
3. The method of claim 2 wherein the pesticidally active ingredient is an insecticide.
4. The method of claim 2 wherein the pesticidally active ingredient is a fungicide.
5. The method of claim 2 wherein the pesticidally active ingredient is a herbicide.
6. The method of claim 1, where the polymer is epoxy.
7. The method of claim 1, wherein the polymer is polymehtylmethacrylate.
8. The method of claim 1, wherein the polymer is polystyrene.
9. The method of claim 1, wherein the polymer is poly (butyl acrylate-co-ethyl acrylate-co-methacrylic acid).

* * * * *